United States Patent [19]  [11] 4,216,318
Brown et al.  [45] Aug. 5, 1980

[54] HETEROCYCLIC ALKYL 4-PYRIMIDONES

[75] Inventors: Thomas H. Brown; Graham J. Durant; Charon R. Ganellin, all of Welwyn Garden City, England

[73] Assignee: Smith Kline & French Laboratories Limited, Welwyn Garden City, England

[21] Appl. No.: 12,640

[22] Filed: Feb. 16, 1979

Related U.S. Application Data

[60] Division of Ser. No. 861,144, Dec. 16, 1977, Pat. No. 4,154,834, which is a continuation-in-part of Ser. No. 753,246, Dec. 22, 1976, abandoned.

[30] Foreign Application Priority Data

Dec. 29, 1975 [GB] United Kingdom ............... 53001/75
Jun. 22, 1977 [GB] United Kingdom ............... 26179/77
Jun. 22, 1977 [GB] United Kingdom ............... 26180/77
Jun. 23, 1977 [GB] United Kingdom ............... 26372/77
Jun. 23, 1977 [GB] United Kingdom ............... 26373/77

[51] Int. Cl.$^2$ ......................................... C07D 401/06

[52] U.S. Cl. .................................. 544/310; 544/238; 544/295; 544/296; 544/319
[58] Field of Search ............... 544/310, 319, 238, 295, 544/296

[56] References Cited

U.S. PATENT DOCUMENTS

| 3,932,644 | 1/1976 | Durant et al. | 544/320 |
| 4,145,546 | 3/1979 | Brown et al. | 544/310 |
| 4,154,834 | 5/1979 | Brown et al. | 544/310 |

Primary Examiner—Paul M. Coughlan, Jr.
Attorney, Agent, or Firm—Joan S. Keps; Richard D. Foggio; William H. Edgerton

[57] ABSTRACT

The compounds are substituted isocytosines which are histamine $H_2$-antagonists. Two specific compounds of the present invention are 2-[2-(5-methyl-4-imidazolylmethylthio)ethylamino]-5-(3-pyridylmethyl)-4-pyrimidone and 2-[2-(3-bromo-2-pyridylmethylthio)ethylamino]-5-(4-pyridylmethyl)-4-pyrimidone.

5 Claims, No Drawings

HETEROCYCLIC ALKYL 4-PYRIMIDONES

This is a division of application Ser. No. 861,144, filed Dec. 16, 1977, U.S. Pat. No. 4,154,834, which is a continuation-in-part of Ser. No. 753,246, filed Dec. 22, 1976, now abandoned.

This invention relates to pharmacologically active compounds, to methods for preparing these compounds, to pharmaceutical compositions containing these compounds and to methods of blocking histamine $H_2$- receptors by administering these compounds. The compounds of the invention can exist as acid addition salts but, for convenience, reference will be made throughout this specification to the parent compounds.

Many physiologically active substances elicit their biological actions by interaction with specific sites known as receptors. Histamine is such a substance and has a number of biological actions. Those biological actions of histamine which are inhibited by drugs commonly called "antihistamines" of which mepyramine, diphenhydramine and chloropheniramine are examples, are mediated through histamine $H_1$- receptors (Ash and Schild, Brit. J. Pharmac. Chemother., 27, 427, (1966)), and drugs with this activity are hereinafter referred to as histamine $H_1$- antagonists. However, other of the biological actions of histamine are not inhibited by histamine $H_1$- antagonists and actions of this type which are inhibited by a compound described by Black et al. (Nature, 236, 385, (1972)) and called burimamide are mediated through receptors which are defined by Black et al. as histamine $H_2$- receptors. Thus histamine $H_2$- receptors may be defined as those histamine receptors which are not blocked by mepyramine but are blocked by burimamide. Compounds which block histamine $H_2$- receptors are referred to as histamine $H_2$- antagonists.

Blockade of histamine $H_2$- receptors is of utility in inhibiting the biological actions of histamine which are not inhibited by histamine $H_1$- antagonists. Histamine $H_2$- antagonists are therefore useful, for example, as inhibitors of gastric acid secretion, as anti-inflammatory agents and as agents which act on the cardiovascular system. The utility of these compounds in blocking histamine $H_2$- receptors in cardiovascular systems can be demonstrated e.g. by inhibiting vasodilation mediated through these receptors. In the treatment of certain conditions for example, inflammation and in inhibiting the actions of histamine on blood pressure, a combination of histamine $H_1$- and $H_2$- antagonists is useful.

The compounds of this invention have both histamine $H_1$- antagonist and histamine $H_2$- antagonist activity, and are useful in the treatment of conditions wherein histamine $H_2$- antagonists are useful and conditions wherein a combination of histamine $H_1$- and $H_2$- antagonists are useful.

The compounds of this invention are represented by the following general formula:

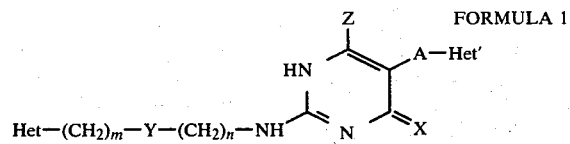

FORMULA 1 wherein Het is 2- or 4-imidazolyl optionally substituted by lower alkyl (preferably methyl), halogen (preferably chlorine or bromine), trifluoromethyl or hydroxymethyl; 2-pyridyl optionally substituted by one or two groups (which may be the same or different) selected from lower alkyl (preferably methyl), lower alkoxy (preferably methoxy), halogen (preferably chlorine or bromine), amino and hydroxy: 2-pyridyl with a phenyl, carbocyclic or cyclic ether ring containing 2 oxygen atoms fused to it: 2-thiazolyl: 3-isothiazolyl optionally substituted by chlorine or bromine: 3-(1,2,5)-thiadiazolyl optionally substituted by chlorine or bromine, or 2-(5-amino-1,3,4-thiadiazolyl): Y is sulphur or a methylene group: m is 0, 1 or 2 and n is 2 or 3 such that their sum is 3 or 4 or when Y is methylene and Het is other than an imidazole ring, 2: Z is hydrogen or lower alkyl (preferably methyl); X is oxygen or sulphur: A is a straight or branched alkylene chain containing from 1–5 carbon atoms or $—(CH_2)_p W(CH_2)_q—$ where W is oxygen or sulphur and p and q are such that their sum is from 1 to 4: Het' is a 5 or 6 membered heterocyclic ring selected from pyridine, pyridine-N-oxide, furan, thiophen, thiazole, oxazole, isothiazole, imidazole, pyrimidine, pyrazine, pyridazine or thiadiazole, which ring is optionally substituted by one or two (which may be the same or different) of the groups selected from lower alkyl, lower alkoxy, halo, hydroxy and amino, or Het' is a pyridine ring with a carbocyclic or cyclic ether ring containing two oxygen atoms fused to it, or Het' is a pyridine, imidazole or thiazole ring which has a benzene ring fused to it: or a pharmaceutically acceptable salt thereof.

Particularly, m is 1 and n is 2.

Preferably Het is 2-thiazolyl, 5-methyl-4-imidazolyl, 5-bromo-4-imidazolyl, 3-bromo-2-pyridyl, 3-chloro-2-pyridyl, 3-methoxy-2-pyridyl, 3-hydroxy-2-pyridyl, 4-methyl-3-bromo-2-pyridyl, or 4-methyl-3-chloro-2-pyridyl.

Preferably Y is sulphur.

Preferably X is oxygen.

Preferably Z is hydrogen.

Preferably A is a straight alkylene chain and is particularly preferably methylene.

Preferably Het' is 2-furyl, 2-thienyl, 2-pyridyl, 3-pyridyl, 4-pyridyl, 2-thiazolyl, 2-imidazolyl, 2-pyrimidyl, 2-pyrazyl or 3-pyridazyl, which ring is optionally substituted by lower alkyl or lower alkoxy. More preferably Het' is 2-thienyl, 2-pyridyl, 3-pyridyl, 4-pyridyl or 2-thiazolyl.

Particularly preferably Het' is 3-pyridyl.

Throughout this specification by the term "lower alkyl" we mean an alkyl group containing from 1 to 4 carbon atoms, and by the term "lower alkoxy" we mean an alkoxy group containing from 1 to 4 carbon atoms.

The compounds of Formula 1 are shown and described as 4-pyrimidone and 4-thione derivatives and these derivatives exist in equilibrium with the corresponding 6-one and 6-thione tautomers. These compounds also exist to a lesser extent as the mercapto and hydroxy tautomers, and the pyrimidine ring may also exist in the following tautomeric forms:

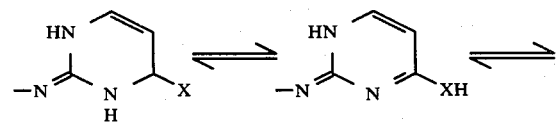

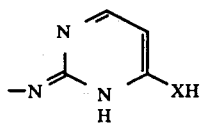

Certain Het and Het' may also exist in several tautomeric forms, and it will be understood that all these tautomeric forms are within the scope of the present invention. Hydrates of compounds of Formula 1 and pharmaceutically acceptable hydrated salts of compounds of Formula 1 are also within the scope of this invention.

Some specific compounds which fall within the scope of the present invention are:

2-[2-(5-methyl-4-imidazolylmethylthio)ethylamino]-5-(4-pyridylmethyl)-4-pyrimidone 2-[2-(2-thiazolylmethylthio)ethylamino]-5-(4-pyridylmethyl)-4-pyrimidone 2-[2-(3-bromo-2-pyridylmethylthio)ethylamino]-5-(4-pyridylmethyl)-4-pyrimidone 2-[2-(5-methyl-4-imidazolylmethylthio)ethylamino]-5-(2-thienylmethyl)-4-pyrimidone 2-[2-(5-methyl-4-imidazolylmethylthio)ethylamino]-5-(2-pyridylmethyl)-4-pyrimidone 2-[2-(5-methyl-4-imidazolylmethylthio)ethylamino]-5-(3-pyridylmethyl)-4-pyrimidone 2-[2-(3-bromo-2-pyridylmethylthio)ethylamino]-5-(2-pyridylmethyl)-4-pyrimidone 2-[2-(5-methyl-4-imidazolylmethylthio)ethylamino]-5-(2-thiazolylmethyl)-4-pyrimidone 2-[2-(2-thiazolylmethylthio)ethylamino]-5-(3-pyridylmethyl)-4-pyrimidone 2-[2-(3-bromo-2-pyridylmethylthio)ethylamino]-5-(3-pyridylmethyl)-4-pyrimidone The compounds of Formula 1 may be prepared by a process which comprises treating an isocytosine of Formula 2

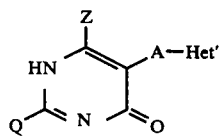

wherein Z, A and Het' are as defined in Formula 1 and Q is loweralkylthio, benzylthio, halogen or other grouping which is conveniently displaced by an amine, with an amine of Formula 3:

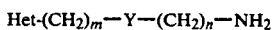

wherein Het, Y, m and n are as defined in Formula 1. Preferably this reaction is carried out in the absence of a solvent at an elevated temperature, e.g., 150° C., or in the presence of a solvent, such as in refluxing pyridine.

Compounds of Formula 1 wherein W is sulphur may alternatively be prepared by a process which comprises treating an isocytosine of Formula 4:

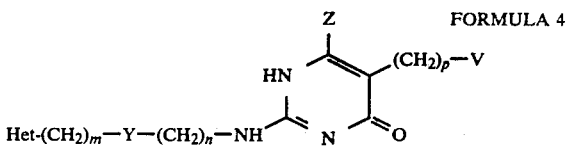

wherein Het, Y, m and n, Z and p are as defined in Formula 1, and V is a mercapto, chloro or bromo group, with a compounds of Formula 5:

wherein Het' is as defined in Formula 1, U is SH when V is chlorio or bromo and U is chloro or bromo when V is mercapto, provided that when U is chloro or bromo, q may only be 0 if U is an 'active' halogen (i.e. ortho or para to a heterocyclic nitrogen atom).

The intermediates of Formula 2 wherein A is an alkylene chain, Z is hydrogen and Q is loweralkylthio (shown as Formula 7) may be prepared according to Scheme 1:

SCHEME 1

(wherein Het' is as defined in Formula 1, a is 0 to 4 and Alk is lower alkyl).

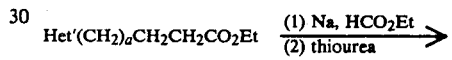

FORMULA 5

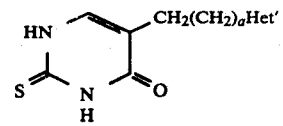

FORMULA 6 alkyl halide
or sulphate

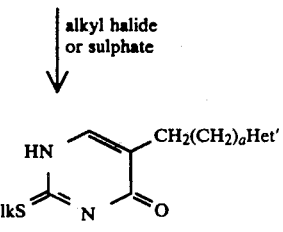

FORMULA 7

The esters of Formula 5 may be prepared by general methods known to the art, for example compounds wherein a is 0 may be prepared by condensing an aldehyde Het'—CHO with malonic acid in the presence of pyridine and piperidine, and hydrogenating and esterifying the product.

The intermediates of Formula 2 wherein A is an alkylene chain, may be made in an analogous way, and the esters of formula Het'—A—CH2CO2Et where A is an alkylene chain may be prepared, for example, by the Wittig reaction, e.g. treating 2-acetylpyridine with carbethoxymethylenetriphenylphosporane.

The intermediates of Formula 2 wherein A is an alkylene chain, Z is lower alkyl, and Q is loweralkylthio (shown as Formula 8) may be prepared according to Scheme 2:

SCHEME 2

(wherein Het' is as defined in Formula 1, a is 0 to 4, Hal is chlorine or bromine, and Alk is lower alkyl).

deprotection, treatment with thionyl chloride, and treatment with the sodium derivative of Het'(CH$_2$)$_q$OH or Het'(CH$_2$)$_q$SH (c) p is 2 to 4

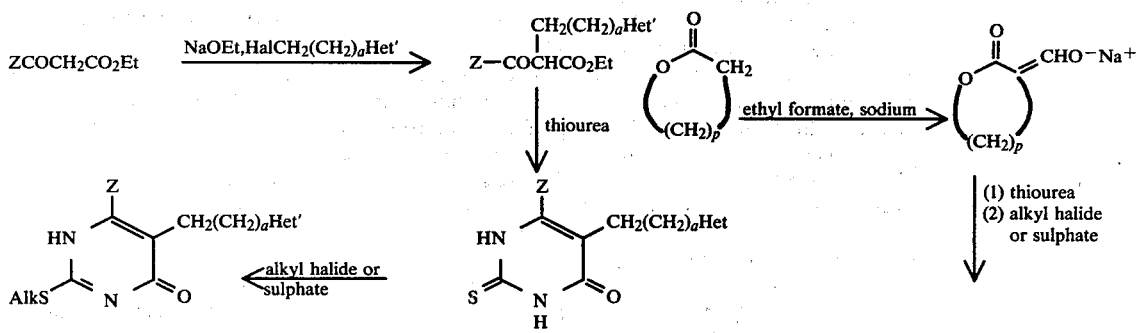

FORMULA 8

The intermediates of Formula 2 wherein Q is halogen and A is an alkylene chain (shown as Formula 10) may be prepared according to Scheme 3:

SCHEME 3

(wherein Het' and Z are as defined in Formula 1, a is 0 to 4 and Hal is chlorine or bromine)

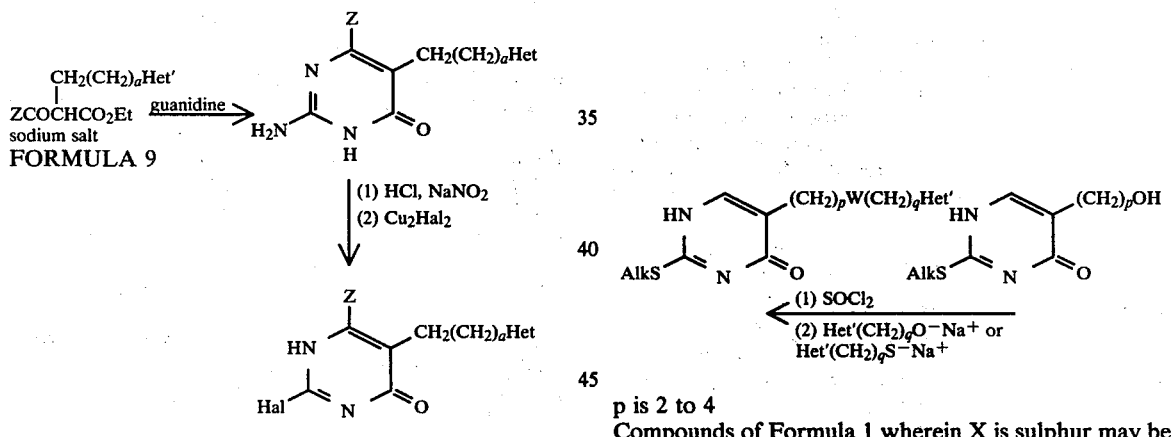

FORMULA 10

The intermediates of Formula 2 wherein A is —(CH$_2$)$_p$W(CH$_2$)$_q$— may be prepared by the following methods:

(a) p is 0
Het'(CH$_2$)$_q$WCH$_2$CO$_2$Et (1) HCO$_2$Et, N
(2) thiourea
(3) alkyl halide or sulphate (b) p is 1

These compounds may be prepared from ethyl 3-benzyloxypropionate, or a similar protected derivative of ethyl 3-hydroxypropionate, by a process analogous to that outlined in Scheme 1, followed successively by deprotection, treatment with thionyl chloride, and treatment with the sodium derivative of Het'(CH$_2$)$_q$OH or Het'(CH$_2$)$_q$SH (c) p is 2 to 4 p is 2 to 4

Compounds of Formula 1 wherein X is sulphur may be prepared by treating the compounds of Formula 1 wherein X is oxygen with phosphorus pentasulphide in a solvent such as pyridine.

The compounds of Formula 1 block histamine H$_2$-receptors, that is they inhibit the biological actions of histamine which are not inhibited by histamine H$_1$-antagonists such as mepyramine but are inhibited by burimamide. For example, the compounds of this invention have been found to inhibit histamine-stimulated secretion of gastric acid from the lumen-perfused stomachs of rats anaesthetised with urethane, at doses of from 0.5 to 16 micromoles per kilogram intravenously. This procedure is referred to in the abovementioned paper of Ash and Schild. The activity of these compounds as histamine H$_2$- antagonists is also demonstrated by their ability to inhibit other actions of histamine which, according to the above mentioned paper of Ash and Schild, are not mediated by histamine H$_1$-receptors. For example, they inhibit the actions of histamine on the isolated guinea pig atrium and isolated rat uterus.

The compounds of this invention inhibit the basal secretion of gastric acid and also that stimulated by pentagastrin or by food.

In addition, in a conventional test such as the measurement of blood pressure in the anaesthetised cat, the action of the compounds of this invention at doses of from 0.5 to 16 micromoles per kilogram intravenously in inhibiting histamine $H_2$- receptor mediated vasodilation can also be demonstrated. The level of activity of the compounds of this invention is illustrated by the effective dose producing 50% inhibition of gastric acid secretion in the anaesthetised rat (which for many of the compounds of Formula 1 is less than 10 micromoles per kilogram) and the dose producing 50% inhibition of histamine-induced tachycardia in the isolated guinea pig atrium (less than $10^{-5}$ Molar).

The compounds of Formula 1 also block histamine $H_1$-receptors, that is they inhibit the biological actions of histamine which are inhibited by mepyramine, diphenhydramine and chlorpheniramine. For example the compounds of this invention have been found to inhibit the action of histamine in the isolated guinea-pig ileum. They inhibit the histamine-stimulated contractions of the guinea-pig ileum at doses of about $10^{-5}$ Molar.

For therapeutic use, the pharmacologically active compounds of the present invention will normally be administered as a pharmaceutical composition comprising as the or an essential active ingredient at least one such compound in the basic form or in the form of an addition salt with a pharmaceutically acceptable acid and in association with a pharmaceutical carrier therefor. Such addition salts include those with hydrochloric, hydrobromic, hydriodic and sulphuric acids and may conveniently be formed from the corresponding bases of Formula 1 by standard procedures, for example by treating the base with an acid in a lower alkanol or by the use of ion exchange resins to form the required salt either directly from the base or from a different addition salt.

Pharmaceutical compositions comprising a pharmaceutical carrier and a compound of Formula 1 or a pharmaceutically acceptable acid addition salt thereof and methods of blocking histamine $H_2$- receptors which comprise administering to an animal a compound of Formula 1 or a pharmaceutically acceptable acid addition salt thereof are also objects of this invention. It is also an object of this invention to provide a method of simultaneously blocking histamine $H_1$- and $H_2$- receptors by administering a compound of Formula 1 or a pharmaceutically acceptable acid addition salt thereof to an animal. The pharmaceutical carrier employed may be, for example, either a solid or liquid. Examplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier will vary widely but preferably will be from about 25 mg to about 1 g. If a liquid carrier is used, the preparation may be in the form of a syrup, emulsion, soft gelatin capsule, sterile injectable liquid contained for example in an ampoule, or an aqueous or non-aqueous liquid suspension.

The pharmaceutical compositions are prepared by conventional techniques involving procedures such as mixing, granulating and compressing or dissolving the ingredients as appropriate to the desired preparation.

The active ingredient will be present in the compositions in an effective amount to block histamine $H_2$- receptors. The route of administration may be oral or parenteral.

Preferably, each dosage unit will contain the active ingredient in an amount of from about 50 mg to about 250 mg.

The active ingredient will preferably be administered one to six times per day. The daily dosage regimen will preferably be from about 150 mg to about 1500 mg.

Advantageously the composition will be made up in a dosage form appropriate to the desired mode of administration for example, as a tablet, capsule, injectable solution or as a cream or ointment for topical application.

The invention is illustrated but in no way limied by the following examples in which all temperatures are in degrees centigrade.

EXAMPLE 1

2-[2-(5-Methyl-4-imidazolylmethylthio)ethylamino]-5-(4-pyridylmethyl)-4-pyrimidone trihydrochloride (i) Ethyl β-(4-pyridyl)propionate (43.45 g) and ethyl formate (19.6 g) were added over a period of 6 hours to a stirred mixture of sodium wire (5.6 g) and dry ether (150 ml) cooled by an ice-salt bath. The mixture was stirred for 18 hours at room temperature, evaporated to dryness and the residue treated with thiourea (18.45 g) and ethanol (130 ml) and refluxed for 7 hours. The mixture was evaporated to dryness and the residue dissolved in water and the solid product precipitated by adding glacial acid to pH4. The white solid was filtered and washed with ethanol to give 5-(4-pyridylmethyl)-2-thiouracil m.p. 320°-324° (decomp).

(ii) A solution of 5-(4-pyridylmethyl)-2-thiouracil (11.0 g), methyl iodide (7.2 g) and sodium hydroxide (2.1 g) in water (50 ml) and ethanol (100 ml) was stirred at 60° for 30 minutes, allowed to cool and filtered to give 5-(4-pyridylmethyl)-2-methylthio-4-pyrimidone m.p. 179°-182° (ethanol).

(iii) An intimate mixture of 5-(4-pyridylmethyl)-2-methylthio-4-pyrimidone (5.9 g) and 2-(5-methyl-4-imidazolylmethylthio)ethylamine (4.3 g) was heated at 145°-150° for 5 hours and allowed to cool to give 2-[2-(5-methyl-4-imidazolylmethylthio)ethylamino]-5-(4-pyridylmethyl)-4-pyrimidone. This residue was triturated with water, and treated with ethanolic hydrogen chloride to give the title compound m.p. 228°-233°.

(Found: C, 43.6; H, 5.1; N, 17.6; S, 7.2; Cl, 21.95; $C_{17}H_{23}Cl_3N_6OS$ requires: C, 43.8: H, 5.0: N, 18.0: S, 6.9: Cl, 22.8%)

EXAMPLE 2

2-[2-(2-Thiazolylmethylthio)ethylamino]-5-(4-pyridylmethyl)-4-pyrimidone trihydrochloride hemihydrate An intimate mixture of 5-(4-pyridylmethyl)-2-methylthio-4-pyrimidone (1.55 g) and 2-(2-thiazolylmethylthio)ethylamine (1.16 g) was heated at 135°-140° with frequent stirring. After cooling, the reaction mixture was triturated under water to give 2-[2-(2-thiazolylmethylthio)ethylamino]-5-(4-pyridylmethyl)-4-pyrimidone. This product was acidified with dilute ethanolic hydrogen chloride, evaporated to dryness and the residue recrystallised from methanol to give the title compound m.p. 190°-195°.

(Found: C. 40.3; H, 4.4; N, 14.5; S, 13.3; Cl, 21.7; $C_{16}H_{17}N_5OS_2.3HCl. \frac{1}{2}H_2O$. Requires: C, 40.2; H, 4.4; N, 14.7; S, 13.4; Cl, 22.3%).

EXAMPLE 3

2-[2-(3-Bromo-2-pyridylmethylthio)ethylamino]-5-(4-pyridylmethyl)-4-pyrimidone dihydrochloride 5-(4-Pyridylmethyl)-2-methylthio-4-pyrimidone (1.1 g) was reacted with 2-(3-bromo-2-pyridylmethylthio)ethylamine (1.15 g) according to the procedure of Example 2. The reaction mixture was triturated under hot water to give 2-[2-(3-bromo-2-pyridylmethylthio)ethylamino]-5-(4-pyridylmethyl)-4-pyrimidone. This product was acidified with dilute ethanolic hydrogen chloride, evaporated to dryness and the residue recrystallised from ethanol to give the title compound m.p. 211°–215° (decomp). (Found: C, 42.65; H, 3.9; N, 13.9; S, 6.3; $C_{18}H_{18}Br N_5OS.2HCl$ requires: C, 42.8; H, 4.0; N, 13.9; S, 6.35%)

EXAMPLE 4

2-[2-(5-Methyl-4-imidazolylmethylthio)ethylamino]-5-(2-thienylmethyl)-4-pyrimidone dihydrochloride (i) Ethyl 2-thienylpropionate (33.3 g), ethyl formate (14.1 g) and sodium (4.2 g) were reacted together in ether (120 ml), the mixture being cooled with an ice-salt bath. The ether was removed by evaporation, and the residue was refluxed with thiourea (13.8 g) and ethanol (100 ml). The ethanol was removed by evaporation and the residue was dissolved in water, and acetic acid was added to precipitate 5-(2-thienylmethyl)-2-thiouracil (38%) m.p. 212°–215° (ethanol).

(ii) 5-(2-Thienylmethyl)-2-thiouracil (4.5 g) was warmed at 65° with a mixture of methyl iodide (2.8 g), sodium hydroxide (0.8 g), water (75 ml) and ethanol (150 ml) to give 5-(2-thienylmethyl)-2-methylthio-4-pyrimidone (89%) m.p. 170.5°–171.5° (ethanol).

(iii) An intimate mixture of 5-(2-thienylmethyl)-2-methylthio-4-pyrimidone (1.43 g) and 2-(5-methyl-4-imidazolylmethylthio)ethylamine (1.03 g) was heated at 140° for 6 hours. The cooled residue was washed with water to give 2-[2-(5-methyl-4-imidazolylmethylthio)ethylamino]-5-(2-thienylmethyl)-4-pyrimidone, and this product was treated with dilute ethanolic HCl to give the title compound in 40% yield, m.p. 172°–176° (ethanol-acetonitrile). The dihydrochloride was passed down an ion-exchange column of IRA 400 eluting with 1 N hydrobromic acid, and the eluate was evaporated to dryness and recrystallised from ethanol acetonitrile to give the corresponding dihydrobromide m.p. 99°–203°. (Found: C, 36.7; H, 4.2; N, 13.5; S, 12.1; Br, 30.6; $C_{16}H_{19}N_5OS_2.2HBr$ Requires: C, 36.7; H, 4.0; N, 13.4; S, 12.2; Br, 30.5%)

EXAMPLE 5

2-[2-(5-methyl-4-imidazolylmethylthio)ethylamino]-5-(2-pyridylmethyl)-4-pyrimidone trihydrochloride hemihydrate (i) Ethyl β-(2-pyridyl)-propionate (19.24 g) and ethyl formate (8.5 g) were added over a period of 1¾ hours to a stirred mixture of sodium wire (2.5 g) and dry ether (80 ml) cooled by a carbon dioxide bath. The mixture was stirred for 21 hours at room temperature, evaporated to dryness and the residue was treated with thiourea (8.2 g) and ethanol (70 ml) and refluxed for 7½ hours. The mixture was evaporated to dryness and the residue was dissolved in water and glacial acid was added to pH 5. The white precipitate was filtered off, washed with water and recrystallised from water-acetic acid to give 5-(2-pyridylmethyl)-2-thiouracil, m.p. 262°–7° (decomp.).

(ii) A solution of 5-(2-pyridylmethyl)-2-thiouracil (6.6 g), methyl iodide (4.3 g) and sodium hydroxide (2.5 g) in water (100 ml) and ethanol (100 ml) was stirred at 70° for 30 minutes, allowed to cool and glacial acetic acid added to pH5. The solution was partially evaporated and cooled in an ice-bath. The precipitate was filtered off and recrystalled from ethanol to give 5-(2-pyridylmethyl)-2-methylthio-4-pyrimidone, m.p. 195°–197.5°.

(iii) An intimate mixture of 5-(2-pyridylmethyl)-2-methylthio-4-pyrimidone (4.7 g) and 2-(5-methyl-4-imidazolylmethylthio)-ethylamine (3.4 g) was heated at 130°–135° for 7 hours. The cooled residue was triturated with hot water to give 2-[2-(5-methyl-4-imidazolylmethythio)ethylamino]-5-(2-pyridylmethyl)-4-pyrimidone and this product was treated with dilue ethanolic HCl to give the title compound m.p. 207°–210° (aqueous ethanol)

(Found: C, 42.8; H, 4.9; N, 17.8; S, 6;9; Cl—, 21.8; $C_{17}H_{20}N_6OS.3HCl.\frac{1}{2}H_2O$ Requires: C, 43.0; H, 5.1; N, 17.7; S, 6.8; Cl—, 22.4%)

EXAMPLE 6

2-[2-(5-Methyl-4-imidazolylmethylthio)-ethylamino]-5-(3-pyridylmethyl)-4-pyrimidone trihydrochloride (i) Ethyl β-(3-pyridyl)-propionate (38.9 g) and ethyl formate (17.0 g) were added over a period of 2¼ hours to a stirred mixture of sodium wire (5.0 g) and dry ether (150 ml) cooled by an ice bath. The mixture was stirred for 22 hours at room temperature, evaporated to dryness and the residue was treated with thiourea (16.5 g) and ethanol (130 ml) and refluxed for 8 hours. The mixture was evaporated to dryness and the residue was dissolved in water and acetic added to pH5 to give 5-(3-pyridylmethyl)-2-thiouracil, m.p. 271°–4° (decomp.) (acetic acid-water)

(ii) A solution of 5-(3-pyridylmethyl)-2-thiouracil (11.0 g), methyl iodide (7.1 g) and sodium hydroxide (4.2 g) in water (150 ml) and ethanol (150 ml) was stirred at 65° for 40 minutes, allowed to cool and acetic acid was added to pH5. The solution was partially evaporated, cooled and filtered to give 5-(3-pyridylmethyl)-2-methylthio-4-pyrimidone, m.p. 247°–9° (ex. ethanol-acetic acid).

(iii) An intimate mixture of 5-(3-pyridylmethyl)-2-methylthio-4-pyrimidone (6.55 g) and 2-(5-methyl-4-imidazolylmethylthio)-ethylamine (4.8 g) was heated at 130°–135° for 7 hours. The cool mixture was triturated with hot water to give 2-[2-(5-methyl-4-imidazolylmethylthio)-ethylamino]-5-(3-pyridylmethyl)-4-pyrimidone and this product was treated with dilute ethanolic HCl to give the title compound m.p. 237°–241° (ethanol-water) (Found: C, 43.7; H, 5.2; N, 17.4; S, 6.5; Cl—22.0. $C_{17}H_{20}N_6OS.3HCl$ requires C, 43.8; H, 5.0; N, 18.0; S, 6.9; Cl, 22.8%)

EXAMPLE 7

2-[2-(3-Bromo-2-pyridylmethylthio)-ethylamino]-5-(2-pyridylmethyl)-4-pyrimidone trihydrobromide An intimate mixture of 5-(2-pyridylmethyl)-2-methylthio-4-pyrimidone (1.5 g) and 2-(3-bromo-2-pyridylmethythio)-ethylamine (1.6 g) was heated at 130° for 6 hours. After cooling, the residue was triturated with hot water and treated with dilute hydrobromic acid to give the title compound, in 44.5% yield, m.p. 225°–230° (decomp.) (ex methanol-water).

(Found: C, 32.1; H, 3.1; N, 10.5; S, 4.8; Br—35.0%. $C_{18}H_{18}BrN_5OS.3HBr$ requires C, 32.0; H, 3.1; N, 10.4; S, 4.8; Br—, 35.5%)

EXAMPLE 8

2-[2-(5-methyl-4-imidazolylmethylthio)-ethylamino]-5-(2-thiazolemethyl)-4-pyrimidone trihydrochloride (i) A solution of 2-thiazoleacrylic acid (26.76 g) and concentrated sulphuric acid (10 ml) in ethanol (150 ml) was refluxed for 18 hours. The solution was partially evaporated and dissolved in water. This solution was extracted with ether and the ethereal extracts were evaporated to give ethyl 2-thiazoleacrylate.

(ii) Ethyl 2-thiazoleacrylate (14.8 g) was dissolved in ethanol (170 ml) and hydrogenated at 40° and a pressure of 50 psi using 10% Palladium on charcoal to give ethyl 2-thiazolepropionate.

(iii) Ethyl 2-thiazolepropionate (14.2 g) and ethyl formate (5.9 g) were added over a period of 2¼ hours to a stirred mixture of sodium wire (1.8 g) and dry ether (65 ml) cooled by an ice-bath. The mixture was stirred for 21 hours at room temperature, evaporated to dryness and the residue was treated with thiourea (5.8 g) and ethanol (60 ml) and refluxed for 9 hours. The solid product was obtained according to the procedure of Example 5(i) to give 5-(2-thiazolemethyl)-2-thiouracil, m.p. 275°–280° (decomp.) (ex acetic acid).

(iv) A solution of 5-(2-thiazolemethyl)-2-thiouracil (4.8 g) methyl iodide (3.0 g.) and sodium hydroxide (0.9 g.) in water (75 ml) and ethanol (150 ml) was stirred at 70° for 30 minutes. The solid product was obtained according to the procedure of Example 5(ii), giving 5-(2-thiazolemethyl)-2-methylthio-4-pyrimidone, m.p. 181°–182.5° (ex ethanol).

(v) An intimate mixture of 5-(2-thiazolemethyl)-2-methylthio-4-pyrimidone (1.4 g) and 2-(5-methyl-4-imidazolylmethylthio)-ethylamine (1.0 g) was heated at 145°–150° for 6 hours. The cooled residue was triturated with hot water to give 2-[2-(5-methyl-4-imidazolylmethylthio)-ethylamino]-5-(2-thiazolemethyl)-4-pyrimidone, and this product was treated with dilute ethanolic HCl to give the title compound m.p. 208°–211° (ex. ethanol water) (Found: C, 38.9; H, 4.7; N, 17.9; S, 13.5; Cl, 21.6. $C_{15}H_{18}N_6OS_2.3HCl$ requires C, 38.2; H, 4.5; N, 17.8; S, 13.6; Cl, 22.5%)

EXAMPLE 9

2-[2-(2-Thiazolylmethylthio)-ethylamino]-5-(3-pyridylmethyl)-4-pyrimidone trihydrobromide 5-(3-Pyridylmethyl)-2-methylthio-4-pyrimidone (1.74 g) was reacted with 2-(2-thiazolylmethylthio)-ethylamine (1.30 g) according to the procedure in Example 2. The reaction mixture was triturated in hot water to give 2-[2-(2-thiazolylmethylthio)-ethylamino]-5-(3-pyridylmethyl)-4-pyrimidone and this product was treated with dilute hydrobromic acid to give the title compound, m.p. 229°–233.5° (ex. methanol-water).

(Found: C, 32.1; H, 3.4; N, 11.7; S, 10.3; Br—, 39.9; $C_{16}H_{17}N_5OS_2.3HBr$ requires: C, 31.9; H, 3.4; N, 11.6; S, 10.7; Br—, 39.8%)

EXAMPLE 10

2-[2-(3-Bromo-2-pyridylmethylthio)-ethylamino]-5-(3-pyridylmethyl)-4-pyrimidone trihydrobromide 5-(3-Pyridylmethyl)-2-methylthio-4-pyrimidone (1.27 g) was reacted with 2-(3-bromo-2-pyridylmethylthio)-ethylamine (1.35 g) according to the procedure in Example 2. The reaction mixture was triturated with hot water to give 2-[2-(3-bromo-2-pyridylmethylthio)-ethylamino]-5-(3-pyridylmethyl)-4-pyrimidone, and this product was treated with dilute hydrobromic acid to give the title compound, m.p. 217°–220.5° (ex-methanol)

(Found: C, 32.1; H, 3.2; N, 10.2; S, 4.5; Br 47.5; $C_{18}H_{18}BrN_5OS.3HBr$ requires: C, 32.0; H, 3.1; N, 10.4; S, 4.8; Br, 47.4%)

EXAMPLE 11

Substitution of
  (a) ethyl β-(2-methoxy-3-pyridyl)propionate
  (b) ethyl β-(3-methoxy-2-pyridyl)propionate
  (c) ethyl β-(3,4-dimethoxy-2-pyridyl)-propionate
  (d) ethyl β-(4-isoquinolyl)propionate
  (e) ethyl β-(2-methyl-5-pyridyl)propionate
  (f) ethyl β-(3,4-dimethyl-2-thiazolyl)-propionate
  (g) ethyl β-(5-methyl-2-thienyl)propionate
for ethyl β-(4-pyridyl)propionate in the procedure of Example 1 leads to the production of
  (a) 2-[2-(5-methyl-4-imidazolylmethylthio)-ethylamino]-5-(2-methoxy-3-pyridylmethyl)-4-pyrimidone
  (b) 2-[2-(5-methyl-4-imidazolylmethylthio)-ethylamino]-5-(3-methoxy-2-pyridylmethyl)-4-pyrimidone
  (c) 2-[2-(5-methyl-4-imidazolylmethylthio)-ethylamino]-5-(3,4-dimethoxy-2-pyridylmethyl)-4-pyrimidone
  (d) 2-[2-(5-methyl-4-imidazolylmethylthio)-ethylamino]-5-(4-isoquinolylmethyl)-4-pyrimidone
  (e) 2-[2-(5-methyl-4-imidazolylmethylthio)-ethylamino]-5-(2-methyl-5-pyridyl)-4-pyrimidone
  (f) 2-[2-(5-methyl-4-imidazolylmethylthio)-ethylamino]-5-(3,4-dimethyl-2-thiazolyl)-4-pyrimidone
  (g) 2-[2-(5-methyl-4-imidazolylmethylthio)-ethylamino]-5-(5-methyl-2-thienyl)-4-pyrimidone The starting materials may be made from the corresponding heterocyclic carboxaldehyde by condensation with malonic acid and subsequent hydrogenation and esterification.

EXAMPLE 12

Substitution of:
  (a) 2-(2-imidazolylmethylthio)ethylamine
  (b) 2-(4-imidazolylmethylthio)ethylamine
  (c) 2-(5-bromo-4-imidazolylmethylthio)-ethylamine
  (d) 2-(5-trifluoromethyl-4-imidazolylmethylthio)ethylamine
  (e) 2-(5-hydroxymethyl-4-imidazolylmethylthio)ethylamine
  (f) 2-(2-pyridylmethylthio)ethylamine
  (g) 2-(3-methyl-2-pyridylmethylthio)ethylamine
  (h) 2-(3-methoxy-2-pyridylmethylthio)-ethylamine
  (i) 2-(3-chloro-2-pyridylmethylthio)-ethylamine
  (j) 2-(3-fluoro-2-pyridylmethylthio)-ethylamine
  (k) 2-(3-iodo-2-pyridylmethylthio)-ethylamine
  (l) 2-(3-amino-2-pyridylmethylthio)-ethylamine (m) 2-(3-hydroxy-2-pyridylmethylthio)-ethylamine
(n) 2-(3-isothiazolylmethylthio)ethylamine
(o) 2-(4-bromo-3-isothiazolylmethylthio)-ethylamine
(p) 2-(3-(1,2,5)-thiadiazolylmethylthio)-ethylamine
(q) 2-(4-chloro-3-(1,2,5)-thiadiazolylmethylthio)ethylamine
(r) 2-(5-amino-2-(1,3,4)-thiadiazolylmethylthio)ethylamine for 2-(5-methyl-4-imidazolylmethylthio)ethylamine in the procedure of Example 6 leads to the production of:
(a) 2-[2-(2-imidazolylmethylthio)ethylamino]-5-(3-pyridylmethyl)-4-pyrimidone
(b) 2-(4-imidazolylmethylthio)ethylamino]-5-(3-pyridylmethyl)-4-pyrimidone
(c) 2-[2-(5-bromo-4-imidazolylmethylthio)ethylamino]-5-(3-pyridylmethyl)-4-pyrimidone
(d) 2-[2-(5-trifluoromethyl-4-imidazolylmethylthio)ethylamino]-5-(3-pyridylmethyl)-4-pyrimidone
(e) 2-[2-(5-hydroxymethyl-4-imidazolylmethylthio)-ethylamino]-5-(3-pyridylmethyl)-4-pyrimidone
(f) 2-[2-(2-pyridylmethylthio)ethylamino]-5-(3-pyridyl-methyl)-4-pyrimidone
(g) 2-[2-(3-methyl-2-pyridylmethylthio)ethylamino]-5-(3-pyridylmethyl)-4-pyrimidone
(h) 2-2-(3-methoxy-2-pyridylmethylthio)ethylamino-5-(3-pyridylmethyl)-4-pyrimidone m.p. 155°–156.5°
(i) 2-2-(3-chloro-2-2-pyridylmethylthio)ethylamino-5-(3-pyridylmethyl)-4-pyrimidone m.p. 134°–135.5°
(j) 2-2-(3-fluoro-2-pyridylmethylthio)ethylamino-5-(3-pyridylmethyl)-4-pyrimidione m.p. 107.5°–109.5°
(k) 2-2-(3-iodo-2-pyridylmethylthio)ethylamino-5-(3-pyridylmethyl)-4-pyrimidone m.p. 111.5°–113.5°
(l) 2-[2-(3-amino-2-pyridylmethylthio)ethylamino]-5-(3-pyridylmethyl)-4-pyrimidone
(m) 2-[2-(3-hydroxy-2-pyridylmethylthio)ethylamino]-5-(3-pyridylmethyl)-4-pyrimidone
(n) 2-[2-(3-isothiazolylmethylthio)ethylamino]-5-(3-pyridylmethyl)-4-pyrimidone
(o) 2-[2-(4-bromo-3-isothiazolylmethylthio)ethylamino]-5-(3-pyridylmethyl)-4-pyrimidone
(p) 2-[2-(3-(1,2,5)-thiadiazolylmethylthio)ethylamino]-5-(3-pyridylmethyl)-4-pyrimidone
(q) 2-[2-(4-chloro-3-(1,2,5)-thiadiazolylmethylthio)ethylamino]-5-(3-pyridylmethyl)-4-pyrimidone
(r) 2-[2-(5-amino-2-(1,3,4)-thiadiazolylmethylthio)ethylamino]-5-(3-pyridylmethyl)-4-pyrimidone

EXAMPLE 13

(i) Reaction of 2-chloro-3-nitropyridine with 2-(2-cyanoethyl)malonic acid diethyl ester and sodium hydride in tetrahydrofuran gives 1-(3-nitro-2-pyridyl)-1,1-bis-(carbethoxy)-butyronitrile, m.p. 93.5°–94.5°, which after alkaline hydrolysis and acidification gives 2-(3-cyanopropyl)-3-nitropyridine hydrochloride 142°–145.5°. Reduction with hydrogen and palladium on charcoal gives 3-amino-2-(3-cyanopropyl)pyridine, and treatment of this with sodium nitrite and sulphuric acid and subsequent warming gives 2-(3-cyanopropyl)-3-hydroxypyridine. Methylation with methyl iodide and sodium ethoxide in dimethylsulphoxide and subsequent reduction with lithium aluminium hydride gives 4-(3-methoxy-2-pyridyl)butylamine. Reduction of 3-amino-2-(3-cyanopropyl)-3-hydroxypyridine with lithium aluminium hydride gives 4-(3-amino-2-pyridyl)-butylamine. Diazotisation of 4-(3-amino-2-pyridyl)-butylamine at pH 1 and treatment was cuprous chloride or cuprous bromide gives 4-(3-chloro-2-pyridyl)butylamine and 4-(3-bromo-2-pyridyl)-butylamine, respectively.

(ii) Substitution of
(a) 4-(4-imidazolyl)butylamine
(b) 4-(3-methoxy-2-pyridyl)-butylamine
(c) 4-(3-chloro-2-pyridyl)-butylamine
(d) 4-(3-bromo-2-pyridyl)butylamine
(e) 4-(3-amino-2-pyridyl)butylamine for 2-(5-methyl-4-imidazolylmethylthio)ethylamine in the procedure of Example 6 leads to the production of:
(a) 2-[4-(4-imidazolyl)butylamino]-5-(3-pyridylmethyl)-4-pyrimidone m.p. 144°–145°
(b) 2-[4-(3-methoxy-2-pyridyl)butylamino]-5-(3-pyridylmethyl)-4-pyrimidone m.p. 117°–118°
(c) 2-[4-(3-chloro-2-pyridyl)butylamino]-5-(3-pyridylmethyl)-4-pyrimidone
(d) 2-[4-(3-bromo-2-pyridyl)butylamino]-5-(3-pyridylmethyl)-4-pyrimidone m.p. 155.5°–157°
(e) 2-[4-(3-amino-2-pyridyl)butylamino]-5-(3-pyridylmethyl)-4-pyrimidone

EXAMPLE 14

Reaction of ethyl acetoacetate with sodium ethoxide and 3-(chloromethyl)pyridine gives ethyl α-(3-pyridylmethyl)acetoacetate which gives 5-(3-pyridylmethyl)-6-methyl-2-thiouracil m.p. 332°–335° when treated with thiourea and sodium ethoxide. Substitution of 5-(3-pyridylmethyl)-6-methyl-2-thiouracil for 5-(4-pyridylmethyl)-2-thiouracil in the general procedure of Example 1 gives 2-[2-(5-methyl-4-imidazolylmethylthio)ethylamino]-5-(3-pyridylmethyl)-6-methyl-4-pyrimidone, m.p. 128°–131°. 5-(3-Pyridylmethyl)-6-methyl-2-methylthio-4-pyrimidone had m.p. 208°–211°.

2-[2-(5-Methyl-4-imidazolylmethylthio)ethylamino]-5-(3-pyridylmethyl)-6-propyl-4-pyrimidone may be prepared in a similar manner starting with ethyl butyroacetate.

EXAMPLE 15

Treatment of 2-[2-(5-methyl-4-imidazolylmethylthio)ethylamino]-5-(3-pyridylmethyl)-4-pyrimidone with phosphorus pentasulphide in hot pyridine leads to the production of 2-[2-(5-methyl-4-imidazolylmethylthio)ethylamino]-5-(3-pyridylmethyl)pyrimid-4-thione.

In a similar manner treatment of the products of Example 12 with phosphorus pentasulphide in hot pyridine leads to the production of:
(a) 2-[2-(2-imidazolylmethylthio)ethylamino]-5-(3-pyridylmethyl)pyrimid-4-thione
(b) 2-(4-imidazolylmethylthio)ethylamino]-5-(3-pyridylmethyl)pyrimid-4-thione
(c) 2-[2-(5-bromo-4-imidazolylmethylthio)ethylamino]-5-(3-pyridylmethyl)pyrimid-4-thione
(d) 2-[2-(5-trifluoromethyl-4-imidazolylmethylthio)ethylamino]-5-(2-pyridylmethyl)pyrimid-4-thione
(e) 2-[2-(5-hydroxymethyl-4-imidazolylmethylthio)ethylamino]-5-(3-pyridylmethyl)pyrimid-4-thione
(f) 2-[2-(2-pyridylmethylthio)ethylamino]-5-(3-pyridylmethyl)pyrimid-4-thione
(g) 2-[2-(3-methyl-2-pyridylmethylthio)ethylamino]-5-(3-pyridylmethyl)pyrimid-4-thione
(h) 2-[2-(3-methoxy-2-pyridylmethylthio)ethylamino]-5-(3-pyridylmethyl)pyrimid-4-thione
(i) 2-[2-(3-chloro-2-pyridylmethylthio)ethylamino]-5-(3-pyridylmethyl)pyrimid-4-thione
(j) 2-[2-(3-amino-2-pyridylmethylthio)ethylamino]-5-(3-pyridylmethyl)pyrimid-4-thione (k) 2-[2-(3-hydroxy-2-pyridylmethylthio)ethylamino]-5-(3-pyridylmethyl)pyrimid-4-thione
(l) 2-[2-(3-isothiazolylmethylthio)ethylamino]-5-(3-pyridylmethyl)pyrimid-4-thione
(m) 2-[2-(4-bromo-3-isothiazolylmethylthio)ethylamino]-5-(3-pyridylmethyl)pyrimid-4-thione
(n) 2-[2-(3-(1,2,5)-thiadiazolylmethylthio)ethylamino]-5-(3-pyridylmethyl)pyrimid-4-thione
(o) 2-[2-(4-chloro-3-(1,2,5)-thiadiazolylmethylthio)ethylamino]-5-(3-pyridylmethyl)pyrimid-4-thione
(p) 2-[2-(5-amino-2-(1,3,4)-thiadiazolylmethylthio)ethylamino]-5-(3-pyridylmethyl)pyrimid-4-thione

EXAMPLE 16

(i) Butyrolactone is treated with sodium and ethyl formate, and the product is successively treated with thiourea and methyl iodide to give 5-(2-hydroxyethyl)-2-methylthio-4-pyrimidone.

(ii) 5-(2-Hydroxyethyl)-2-methylthio-4-pyrimidone is treated with thionyl chloride and the product is reacted with the sodium derivative of (a) 3-hydroxymethyl)-pyridine and (b) 3-(mercaptomethyl)pyridine to give:
    (a) 5-(2-(3-pyridylmethoxy)ethyl)-2-methylthio-4-pyrimidone
    (b) 5-(2-(3-pyridylmethylthio)ethyl)-2-methylthio-4-pyrimidone (iii) substitution of:
    (a) 5-(2-(3-pyridylmethoxy)ethyl)-2-methylthio-4-pyrimidone
    (b) 5-(2-(3-pyridylmethylthio)ethyl)-2-methylthio-4-pyrimidone
for 5-(3-pyridylmethyl)-2-methylthio-4-pyrimidone in the general procedure of Example 6 leads to the production of:
    (a) 2-[2-(5-methyl-4-imidazolylmethylthio)ethylamino]-5-(2-(3-pyridylmethoxy)ethyl)-4-pyrimidone
    (b) 2-[2-(5-methyl-4-imidazolylmethylthio)ethylamino]-5-(2-(3-pyridylmethylthio)ethyl)-4-pyrimidone (iv) substitution of:
    (a) 3-hydroxypyridine and
    (b) 3-mercaptopyridine for
3-(hydroxymethyl)pyridine in procedure (ii) and (iii) above leads to the production of:
    (a) 2-[2-(5-methyl-4-imidazolylmethylthio)ethylamino]-5-(2-(3-pyridyloxy)ethyl)-4-pyrimidone
    (b) 2-[2-(5-methyl-4-imidazolylmethylthio)ethylamino]-5-(2-(3-pyridylthio)ethyl)-4-pyrimidone (v) substitution of:
    (a) 3-(2-hydroxyethyl)pyridine and
    (b) 3-(2-mercaptoethyl)pyridine for
3-(hydroxymethyl)pyridine in procedure (ii) and (iii) above leads to the production of
    (a) 2-[2-(5-methyl-4-imidazolylmethylthio)ethylamino]-5-(2-(2-(3-pyridyl)ethoxy)ethyl)-4-pyrimidone
    (b) 2-[2-(5-methyl-4-imidazolylmethylthio)ethylamino]-5-(2-(2-(3-pyridyl)ethylthio)ethyl)-4-pyrimidone (vi) substitution of caprolactone for butyrolactone in procedure (i) (ii) and (iii) above leads to the production of
    (a) 2-[2-(5-methyl-4-imidazolylmethylthio)ethylamino]-5-(3-(3-pyridylmethoxy)propyl)-4-pyrimidone
    (b) 2-[2-(5-methyl-4-imidazolylmethylthio)ethylamino]-5-(3-(3-pyridylmethylthio)propyl)-4-pyrimidone

EXAMPLE 17

Ethyl 3-pyridylmethoxyacetate is converted into 5-(3-pyridylmethoxy)-2-thiouracil by the general procedure of Example 1 (i). Substitution of 5-(3-pyridylmethoxy)-2-thiouracil for 5-(4-pyridylmethyl)-2-thiouracil in the general procedure of Example 1 gives 2-[2-(5-methyl-4-imidazolylmethylthio)ethylamino]-5-(3-pyridylmethoxy)-4-pyrimidone.

2-[2-(5-Methyl-4-imidazolylmethylthio)ethylamino]-5-(3-(3-pyridylpropoxy)-4-pyrimidone and 2-[2-(5-methyl-4-imidazolylmethylthio)ethylamino]-5-(3-(3-pyridyl)propylthio)-4-pyrimidone may be prepared in a similar manner starting with ethyl 3-(3-pyridyl)propoxyacetate and ethyl 3-(3-pyridyl)propylthioglycolate, respectively.

EXAMPLE 18

Substitution of
    (a) ethyl β-(2-furyl)propionate
    (b) ethyl β-(5-oxazolyl)propionate
    (c) ethyl β-(3-isothiazolyl)propionate
    (d) ethyl β-(2-pyrimidyl)propionate
    (e) ethyl β-(5-pyrimidyl)propionate
    (f) ethyl β-(2-pyrazyl)propionate
    (g) ethyl β-(4-pyridazyl)propionate
for ethyl β-(4-pyridyl)propionate in the procedure of Example 1 leads to the production of
    (a) 2-[2-(5-methyl-4-imidazolylmethylthio)ethylamino]-5-(2-furylmethyl)-4-pyrimidone
    (b) 2-[2-(5-methyl-4-imidazolylmethylthio)ethylamino]-5-(2-oxazolylmethyl)-4-pyrimidone
    (c) 2-[2-(5-methyl-4-imidazolylmethylthio)ethylamino]-5-(3-isothiazolylmethyl)-4-pyrimidone
    (d) 2-[2-(5-methyl-4-imidazolylmethylthio)ethylamino]-5-(2-pyrimidylmethyl)-4-pyrimidone
    (e) 2-[2-(5-methyl-4-imidazolylmethylthio)ethylamino]-5-(5-pyrimidylmethyl)-4-pyrimidone
    (f) 2-[2-(5-methyl-4-imidazolylmethylthio)ethylamino]-5-(2-pyrazylmethyl)-4-pyrimidone
    (g) 2-[2-(5-methyl-4-imidazolylmethylthio)ethylamino]-5-(4-pyridazylmethyl)-4-pyrimidone
The starting materials (b) to (g) above may be prepared by condensing the corresponding heterocyclic carboxaldehyde with malonic acid, and hydrogenating and esterifying the product.

EXAMPLE 19

Treatment of 1-(4-methoxybenzyl)-2-imidazole carboxyaldehyde with malonic acid in the presence of pyridine and piperidine gives 2-[1-(4-methoxybenzyl)imidazolyl]acrylic acid. Substitution of 2-[1-(4-methoxybenzyl)imidazolyl]acrylic acid for 2-thiazoleacrylic acid in the procedure of Example 8 and deprotection of the product with anisole and hydrogen bromide in acetic acid gives 2-[2-(5-methyl-4-imidazolylmethylthio)ethylamino]-5-(2-imidazolylmethyl)-4-pyrimidone.

EXAMPLE 20

2-[2-(5-methyl-4-imidazolylmethylthio)-ethylamino]-5-(3-quinolylmethyl)-4-pyrimidone trihydrochloride (i) A solution of 3-quinolineacrylic acid (63.71 g) and concentrated sulphuric acid (25 ml) in ethanol (350 ml) was refluxed for 18 hours. The product was obtained according to the procedure of Example 8 (i), giving ethyl 3-quinolineacrylate, m.p. 86.5°–88° (Ex ethanol-water).

(Found: C, 73.8; H, 5.8; N, 6.0; $C_{14}H_{13}NO_2$ requires: C, 74.0; H, 5.8; N, 6.2%)

(ii) 3-quinolineacrylate (51.68 g) was dissolved in ethanol (170 ml) and hydrogenated at 37° and a pressure of 50 psi using 10% Palladium on charcoal to give ethyl 3-quinolinepropionate. p (iii) Ethyl 3-quinolinepropionate (47.99 g) and ethyl formate (16.3 g) were added over a period of 3 hours to a stirred mixture of sodium wire (4.8 g) and dry ether (150 ml) cooled by an ice-bath. The mixture was stirred for 20 hours at room temperature, evaporated to dryness and the residue was treated with thiourea (15.9 g) and ethanol (130 ml) and refluxed for 7 hours. The mixture was evaporated to dryness and the residue was dissolved in water and acetic acid added to pH 4. The mixture was filtered to give 5-(3-quinolinemethyl)-2-thiouracil, m.p. 281°–6° (decomp.) (ex. acetic acid-water).

(iv) A solution of 5-(3-quinolinemethyl)-2-thiouracil (17.51 g), methyl iodide (9.2 g) and sodium hydroxide (5.4 g) in water (200 ml) and ethanol (200 ml) was stirred at 75° for 1 hour, allowed to cool and acetic acid added to pH 4 to give 5-(3-quinolinemethyl)-2-methylthio-4-pyrimidone, m.p. 215.5°–218° (ex. ethanol).

(v) An intimate mixture of 5-(3-quinolinemethyl)-2-methylthio-4-pyrimidone (2.1 g) and 2-(5-methyl-4-imidazolylmethylthio)-ethylamine (1.3 g) was heated at 150°–5° for 6 hours. The cooled mixture was triturated with hot water and treated with dilute ethanolic HCl to give the title compound, m.p. 184°–9° (ex. ethanol-water).

EXAMPLE 21

2-[2-(2-thiazolylmethylthio)ethylamino]-5-(3-quinolylmethyl)-4-pyrimidone trihydrochloride An intimate mixture of 5-(3-quinolinemethyl)-2-methylthio-4-pyrimidone (2.0 g) and 2-(2-thiazolylmethylthio)-ethylamine (1.2 g) was heated at 145° for 4 hours. After cooling the residue was triturated with hot water and treated with dilute ethanolic HCl to give the title compound, m.p. 217.5°–221.5° (ex. ethanol-water).

(Found: C, 45.9; H, 4.3; N, 13.3; S, 12.2; Cl, 19.7 $C_{20}H_{19}N_5OS_2.3HCl$ requires: C, 46.3; H, 4.3; N, 13.5; S, 12.4; Cl, 20.5%)

EXAMPLE 22

2-[2-(3-Bromo-4-methyl-2-pyridylmethylthio)ethylamino]-5-(3-pyridylmethyl)-4-pyrimidone (a) Oleum (65%, 600 ml) was carefully added to cold 2,4-dimethylpyridine (107.4 g). Bromine (80 g) was added and the mixture was heated for 20 hours at 55°, allowed to cool and poured on to ice. The mixture was neutralised with aqueous sodium hydroxide and extracted with ether. The ether extracts were stirred with ferrous sulphuric overnight, evaporated and the residue was distilled to give a mixture of 3-bromo-2,4-dimethylpyridine and 5-bromo-2,4-dimethylpyridine (66.6 g, b.p. 88°–90° at 11 mm Hg).

(b) A portion of this mixture (54 g) was added to a stirred solution of 3-chloroperbenzoic acid (60 g) in chloroform (500 ml) maintained at 20°–25°. The mixture was stirred for 2 hours and ammonia was bubbled into the cooled mixture. The mixture was filtered, and the filtrate was evaporated to a residue which was twice recrystallised from ethyl acetate to give 3-bromo-2,4-dimethylpyridine-N-oxide (15.7 g) m.p. 157°–158°.

Found: C, 41.7; H, 4.0; N, 7.1; Br, 39.9; $C_7H_5BrNO$. Requires: C, 4.16; H, 4.0; N, 6.9; Br, 39.6%

(c) 3-Bromo-2,4-dimethylpyridine-N-oxide (14.7 g) in warm acetic anhydride (150 ml) was added dropwise to acetic anhydride (500 ml) at 125° and the mixture was refluxed for ½ hour, allowed to cool and then poured into water/ethanol (4:1, 500 ml). The solution was acidified with dilute hydrochloric acid and evaporated to dryness. The residue was refluxed with 2 N hydrochloric acid (100 ml) for 1 hour, cooled and extracted with chloroform. The aqueous phase was adjusted to pH 12 with sodium hydroxide and was extracted with chloroform, and this chloroform extract was evaporated to a residue which was crystallised from n-hexane to give 3-bromo-2-hydroxymethyl-4-methylpyridine (5.8 g) m.p. 75°–77°.

Found: C, 41.8; H, 4.0; N, 7.0; Br, 39.3; $C_7H_5BrNO$. Requires: C, 41.6; H, 4.0; N, 6.9; Br, 39.6%

(d) A mixture of 3-bromo-2-hydroxymethyl-4-methylpyridine (5.8), cysteamine hydrochloride (3.5 g) and hydrobromic acid (48%, 50 ml) was refluxed for 6 hours and evaporated to dryness. The residue was crystallised from isopropanol/methanol to give 2-(3-bromo-4-methyl-2-pyridylmethylthio)ethylamine dihydrobromide (8.5 g) m.p. 203°–205°.

Found: C, 25.5; H, 3.6; N, 6.5; S, 7.6; Br, 56.6; $C_9H_{13}BrN_2S.2HBr$. Requires: C, 25.5; H, 3.6; N, 6.6; S, 7.6; Br, 56.7%

(e) 2-(3-Bromo-4-methyl-2-pyridylmethylthio)ethylamine (1.5 g) and 5-(3-pyridylmethyl)-2-methylthio-4-pyrimidone (1.0 g) were fused together at 160°–170° for 1 hour. The cool mixture was taken up in water at pH 2 and extracted with chloroform. The aqueous phase was adjusted to pH 7 and extracted with chloroform, and the chloroform extract was evaporated and the residue purified chromatographically on silica gel (eluting with chloroform/ammoniacal methanol (50:1) to give the title compound, m.p. 81°–85°.

Found: C, 49.5; H, 4.9; N, 15.1; S, 7.0; Br, 17.7; $C_{19}H_{20}BrN_5OS.0.8H_2O$. Requires: C, 49.5; H, 4.7; N, 15.2; S, 7.0; Br, 17.3%

EXAMPLE 23

Substitution of
  (a) ethyl β-(4,5-dimethoxy-2-pyridyl)propionate
  (b) ethyl β-(4-hydroxy-5-methoxy-2-pyridyl)propionate
  (c) ethyl β-(4-hydroxy-3-methoxy-2-pyridyl)propionate
  (d) ethyl β-(4,6-dimethoxy-3-pyridyl)-propionate
  (e) ethyl β-(2,6-dimethoxy-4-pyridyl)-propionate
  (f) ethyl β-(4,5-dimethyl-2-thienyl)-propionate
for ethyl β-(3-pyridyl)propionate in the procedure of Example 6 and fusion of the resultant 2-methylthio-4-pyrimidones with 2-(5-methyl-4-imidazolylmethylthio)-ethylamine gives
  (a) 2-[2-(5-methyl-4-imidazolylmethylthio)ethylamino]-5-(4,5-dimethoxy-2-pyridylmethyl)-4-pyrimidone
  (b) 2-[2-(5-methyl-4-imidazolylmethylthio)ethylamino]-5-(4-hydroxy-5-methoxy-2-pyridylmethyl)-4-pyrimidone
  (c) 2-[2-(5-methyl-4-imidazolylmethylthio)ethylamino]-5-(4-hydroxy-3-methoxy-2-pyridylmethyl)-4-pyrimidone (d) 2-[2-(5-methyl-4-imidazolylmethylthio)e-thylamino]-5-(4,6-dimethoxy-3-pyridylmethyl)-4-pyrimidone (e) 2-[2-(5-methyl-4-imidazolylmethylthio)e-thylamino]-5-(2,6-dimethoxy-4-pyridylmethyl)-4-pyrimidone (f) 2-[2-(5-methyl-4-imidazolylmethylthio)e-thylamino]-5-(4,5-dimethyl-2-thienylmethyl)-4-pyrimidone The starting materials may be prepared by condensing the corresponding heterocyclic carboxaldehyde with malonic acid, and hydrogenating and esterifying the products, or by treating a halomethylheterocyclic derivative with sodium and diethyl malonate.

EXAMPLE 24

Substitution of
(a) ethyl β-(5-amino-2-pyridyl)propionate
(b) ethyl β-(6-amino-3-pyridyl)propionate
(c) ethyl β-(2-(5-amino-1,3,4-thiadiazolyl))-propionate for ethyl β-(3-pyridyl)propionate in the procedure of Example 6 and fusion of the resultant 2-methylthio-4-pyrimidones with 2-(5-methyl-4-imidazolylmethylthio)-ethylamine gives (a) 2-[2-(5-methyl-4-imidazolylmethylthio)e-thylamino]-5-(5-amino-2-pyridylmethyl)-4-pyrimidone
(b) 2-[2-(5-methyl-4-imidazolylmethylthio)e-thylamino]-5-(6-amino-3-pyridylmethyl)-4-pyrimidone
(c) 2-[2-(5-methyl-4-imidazolylmethylthio)e-thylamino]-5-(2-(5-amino-(1,3,4)thiadiazolyl)methyl)-4-pyrimidone

EXAMPLE 25

2,3-Dimethylpyridine is treated with bromine in oleum to give 3-bromo-5,6-dimethylpyridine which is converted into a Grignard reagent, and this is treated with ethyl orthoformate and the product hydrolysed to give 5,6-dimethylpyridine-3-carboxaldehyde. This aldehyde is condensed with malonic acid and the product is hydrogenated and esterified to give ethyl β-(5,6-dimethyl-3-pyridyl)propionate. Substitution of this ester for ethyl β-(3-pyridyl)propionate in the procedure of Example 6 and fusion of the product with 2-(5-methyl-4-imidazolylmethylthio)ethylamine gives 2-[2-(5-methyl-4-imidazolylmethylthio)ethylamino]-5-(5,6-dimethyl-3-pyridylmethyl)-4-pyrimidone.

EXAMPLE 26

Substitution of
(a) ethyl β-(3-chloro-2-pyridyl)propionate
(b) ethyl β-(4-bromo-3-isothiazolyl)propionate
(c) ethyl β-(4-bromo-2-imidazolyl)propionate
(d) ethyl β-(2-bromo-5-thiazolyl)propionate
(e) ethyl β-(4-hydroxy-2-pyrimidyl)propionate for ethyl β-(3-pyridyl)propionate in the procedure of Example 6 and fusion of the product with 2-(5-methyl-4-imidazolylmethylthio)ethylamine gives (a) 2-[2-(5-methyl-4-imidazolylmethylthio)e-thylamino]-5-(3-chloro-2-pyridylmethyl)-4-pyrimidone
(b) 2-[2-(5-methyl-4-imidazolylmethylthio)e-thylamino]-5-(4-bromo-3-isothiazolylmethyl)-4-pyrimidone
(c) 2-[2-(5-methyl-4-imidazolylmethylthio)e-thylamino]-5-(4-bromo-2-imidazolylmethyl)-4-pyrimidone
(d) 2-[2-(5-methyl-4-imidazolylmethylthio)e-thylamino]-5-(2-bromo-5-thiazolylmethyl)-4-pyrimidone
(e) 2-[2-(5-methyl-4-imidazolylmethylthio)e-thylamino]-5-(4-hydroxy-2-pyrimidylmethyl)-4-pyrimidone

EXAMPLE 27

Substitution of
(a) 4-hydroxymethyl-(1,3)-dioxolo[4,5-C]pyridine
(b) 2,3-dihydro-5-hydroxymethyl(p-dioxino[2,3-C]pyridine)
(c) 3,4-dimethoxy-2-hydroxymethylpyridine
(d) 5,6,7,8-tetrahydro-1-hydroxymethylisoquinoline
(e) 1-hydroxymethyl-isoquinoline for 3-bromo-2-hydroxymethyl-4-methylpyridine in the procedure of Example 22 (d,e) gives (a) 2-[2-(4-(1,3-dioxolo[4,5-C]pyridyl)methylthio)e-thylamino]-5-(3-pyridylmethyl)-4-pyrimidone
(b) 2-[2-(5-(2,3-dihydro-p-dioxino[2,3-C]pyridyl)methylthio)-ethylamino]-5-(3-pyridylmethyl-4-pyrimidone
(c) 2-[2-(3,4-dimethoxy-2-pyridylmethylthio)e-thylamino]-5-(3-pyridylmethyl)-4-pyrimidone
(d) 2-[2-(5,6,7,8-tetrahydro-1-isoquinolyl)e-thylamino]-5-(3-pyridylmethyl)-4-pyrimidone
(e) 2-2-(1-isoquinolyl)ethylamino-5-(3-pyridylmethyl)-4-pyrimidone

EXAMPLE 28

Substitution of
(a) ethyl 3-(3-pyridyl)butanoate
(b) ethyl 3-(3-methoxy-2-pyridyl)butanoate
(c) ethyl 4-(3-pyridyl)pentanoate
(d) ethyl 4-(3-methoxy-2-pyridyl)pentanoate
(e) ethyl β-(2-benzimidazolyl)propionate
(f) ethyl β-(2-benzthiazolyl)propionate
(g) ethyl β-(4,-(1,3-dioxolo[4,5-C]pyridyl)propionate
(h) ethyl β-(5-(2,3-dihydro-p-dioxino[2,3-C]pyridyl)-propionate
(i) ethyl β-(5,6,7,8-tetrahydro-1-isoquinolyl)propionate for ethyl β-(4-pyridyl)propionate in the procedure of Example 1 leads to the production of (a) 2-[2-(5-methyl-4-imidazolylmethylthio)e-thylamino]-5-(1-(3-pyridyl)ethyl)-4-pyrimidone
(b) 2-[2-(5-methyl-4-imidazolylmethylthio)e-thylamino]-5-(1-(3-methoxy-2-pyridyl)ethyl)-4-pyrimidone
(c) 2-[2-(5-methyl-4-imidazolylmethylthio)e-thylamino]-5-(2-(3-pyridyl)propyl)-4-pyrimidone
(d) 2-[2-(5-methyl-4-imidazolylmethylthio)e-thylamino]-5-(2-(3-methoxy-2-pyridyl)propyl)-4-pyrimidone
(e) 2-[2-(5-methyl-4-imidazolylmethylthio)e-thylamino]-5-(2-benzimidazolylmethyl)-4-pyrimidone
(f) 2-[2-(5-methyl-4-imidazolylmethylthio)e-thylamino]-5-(2-benzthiazolylmethyl)-4-pyrimidone
(g) 2-[2-(5-methyl-4-imidazolylmethylthio)e-thylamino]-5-(4-(1,3-dioxolo[4,5-C]pyridyl)methyl)-4-pyrimidone (h)  2-[2-(5-methyl-4-imidazolylmethylthio)ethylamino]-5-(5-(2,3-dihydro-p-dioxino[2,3-C]pyridyl)methyl-4-pyrimidone
(i)  2-[2-(5-methyl-4-imidazolylmethylthio)ethylamino]-5-(5,6,7,8-tetrahydro-1-isoquinolylmethyl)-4-pyrimidone

EXAMPLE 29

Pharmaceutical composition:

| Ingredients | Amounts |
| --- | --- |
| 2-[2-(5-methyl-4-imidazolymethylthio)-ethylamino]-5-(3-pyridylmethyl)-4-pyrimidone trihydrochloride | 75 mg |
| Sucrose | 75 mg |
| Starch | 25 mg |
| Talc | 5 mg |
| Stearic Acid | 2 mg |

The ingredients are screened, mixed and filled into a hard gelatin capsule.

EXAMPLE 30

Pharmaceutical composition:

| Ingredients | Amounts |
| --- | --- |
| 2-[2-(5-methyl-4-imidazolylmethylthio)-ethylamino]-5-(3-pyridylmethyl)-4-pyrimidone trihdrochloride | 100 mg |
| Lactose | 100 mg |

The ingredients are screened, mixed and filled into a hard gelatin capsule.

Similarly, the other compounds of Formula 1 may be formulated into pharmaceutical compositions by the procedures of Examples 29 and 30.

The pharmaceutical compositions prepared as in the foregoing examples are administered to a subject within the dose ranges given hereabove to block histamine $H_2$-receptors.

EXAMPLE 31

2-[3-(5-Methyl-4-imidazolylmethylthio)propylamino]-5-(4-pyridylmethyl)-4-pyrimidone trihydrochloride (i) An intimate mixture of 5-(4-pyridylmethyl)-2-methylthio-4-pyrimidone and 3-(5-methyl-4-imidazolylmethylthio)propylamine are heated at 145°-150° for 5 hours and allowed to cool. The residue is triturated with water, and treated with ethanolic hydrogen chloride to give the title compound.

(ii) In a similar manner 2-[3-(5-methyl-4-imidazolylmethylthio)propylamino]-5-(3-pyridylmethyl)-4-pyrimidone trihydrochloride m.p. 184°-189° was prepared from 5-(3-pyridylmethyl-2-methylthio-4-pyrimidone.

EXAMPLE 32

2-[3-(2-Thiazolylmethylthio)propylamino]-5-(4-pyridylmethyl)-4-pyrimidone trihydrochloride An intimate mixture of 5-(4-pyridylmethyl)-2-methylthio-4-pyrimidone and 3-(2-thiazolylmethylthio)propylamine is heated at 135°-140° with frequent stirring. After cooling, the reaction mixture is triturated under water, acidified with dilute ethanolic hydrogen chloride, evaporated to dryness and the residue is recrystallised from methanol to give the title compound.

EXAMPLE 33

2-[3-(3-Bromo-2-pyridylmethylthio)propylamino]-5-(4-pyridylmethyl)-4-pyrimidone dihydrochloride 5-(4-Pyridylmethyl)-2-methylthio-4-pyrimidone is reacted with 3-(3-bromo-2-pyridylmethylthio)propylamine (1.15 g) according to the procedure of Example 32. The reaction mixture is triturated under hot water, acidified with dilute ethanolic hydrogen chloride, evaporated to dryness and the residue recrystallised from ethanol to give the title compound.

EXAMPLE 34

2-[3-(5-Methyl-4-imidazolylmethylthio)propylamino]-5-(2-thienylmethyl)-4-pyrimidone dihydrochloride An intimate mixture of 5-(2-thienylmethyl)-2-methylthio-4-pyrimidone and 3-(5-methyl-4-imidazolylmethylthio)propylamine is heated at 140° for 6 hours. The cooled residue is washed with water and treated with dilute ethanolic HCl to give the title compound. The dihydrochloride is passed down an ion-exchange column of IRA 400 eluting with 1 N hydrobromic acid, and the eluate is evaporated to dryness and recrystallised to give the corresponding dihydrobromide.

EXAMPLE 35

2-[2-(5-Methyl-4-imidazolylmethylthio)propylamino]-5-(2-pyridylmethyl)-4-pyrimidone trihydrochloride An intimate mixture of 5-(2-pyridylmethyl)-2-methylthio-4-pyrimidone and 3-(5-methyl-4-imidazolylmethylthio)propylamine is heated at 130°-135° for 7 hours. The cooled residue is triturated with hot water and treated with dilute ethanolic HCl to give the title compound.

EXAMPLE 36

2-[3-(5-Methyl-4-imidazolylmethylthio)propylamino]-5-(3-pyridylmethyl)-4-pyrimidone An intimate mixture of 5-(3-pyridylmethyl)-2-methylthio-4-pyrimidone and 3-(5-methyl-4-imidazolylmethylthio)propylamine is heated at 130°-135° for 7 hours. The cool mixture is triturated with hot water and treated with dilute ethanolic HCl to give the trihydrochloride of the title compound.

EXAMPLE 37

Substitution of
(a) ethyl β-(2-methoxy-3-pyridyl)propionate
(b) ethyl β-(3-methoxy-2-pyridyl)propionate
(c) ethyl β-(3,4-dimethoxy-2-pyridyl)propionate
(d) ethyl β-(3-quinolyl)propionate
(e) ethyl β-(4-isoquinolyl)propionate
for ethyl β-(4-pyridyl)propionate in the procedure of Example 31, leads to the production of:
(a)  2-[3-(5-methyl-4-imidazolylmethylthio)-propylamino]-5-(2-methoxy-3-pyridylmethyl)-4-pyrimidone
(b)  2-[3-(5-methyl-4-imidazolylmethylthio)-propylamino]-5-(3-methoxy-2-pyridylmethyl)-4-pyrimidone
(c)  2-[3-(5-methyl-4-imidazolylmethylthio)-propylamino]-5-(3,4-dimethoxy-2-pyridylmethyl)-4-pyrimidone
(d)  2-[3-(5-methyl-4-imidazolylmethylthio)-propylamino]-5-(3-quinolylmethyl)-4-pyrimidone (e) 2-[3-(5-methyl-4-imidazolylmethylthio)-propylamino]-5-(4-isoquinolylmethyl)-4-pyrimidone The starting materials may be made from the corresponding heterocyclic carboxaldehyde by condensation with malonic acid and subsequent hydrogenation and esterification.

EXAMPLE 38

Substitution of:
(a) 3-(2-imidazolylmethylthio)propylamine
(b) 3-(4-imidazolylmethylthio)propylamine
(c) 3-(5-bromo-4-imidazolylmethylthio)-propylamine
(d) 3-(5-trifluoromethyl-4-imidazolylmethylthio)-propylamine
(e) 3-(5-hydroxylmethyl-4-imidazolylmethylthio)-propylamine
(f) 3-(2-pyridylmethylthio)propylamine
(g) 3-(3-methyl-2-pyridylmethylthio)-propylamine
(h) 3-(3-methoxy-2-pyridylmethylthio)-propylamine
(i) 3-(3-chloro-2-pyridylmethylthio)-propylamine
(j) 3-(3-amino-2-pyridylmethylthio)-propylamine
(k) 3-(3-hydroxy-2-pyridylmethylthio)-propylamine
(l) 3-(3-isothiazolylmethylthio)propylamine
(m) 3-(4-bromo-3-isothiazolylmethylthio)-propylamine
(n) 3-(3-(1,2,5)-thiadiazolylmethylthio)-propylamine
(o) 3-(4-chloro-3-(1,2,5)-thiadiazolylmethylthio)-propylamine
(p) 3-(5-amino-2-(1,3,4)-thiadiazolylmethylthio)-propylamine for 3-(5-methyl-4-imidazolylmethylthio)propylamine in the procedure of Example 36 leads to the production of:
(a) 2-[3-(2-imidazolylmethylthio)propylamino]-5-(3-pyridylmethyl)-4-pyrimidone
(b) 2-[3-(4-imidazolylmethylthio)propylamino]-5-(3-pyridylmethyl)-4-pyrimidone
(c) 2-[3-(5-bromo-4-imidazolylmethylthio)-propylamino]-5-(3-pyridylmethyl)-4-pyrimidone
(d) 2-[3-(5-trifluoromethyl-4-imidazolylmethylthio)-propylamino]-5-(3-pyridylmethyl)-4-pyrimidone
(e) 2-[3-(5-hydroxymethyl-4-imidazolylmethylthio)-propylamino]-5-(3-pyridylmethyl)-4-pyrimidone
(f) 2-[3-(2-pyridylmethylthio)propylamino]-5-(3-pyridylmethyl)-4-pyrimidone
(g) 2-[3-(3-methyl-2-pyridylmethylthio)-propylamino]-5-(3-pyridylmethyl)-4-pyrimidone
(h) 2-[3-(3-methoxy-2-pyridylmethylthio)-propylamino]-5-(3-pyridylmethyl)-4-pyrimidone
(i) 2-[3-(3-chloro-2-pyridylmethylthio)propylamino]-5-(3-pyridylmethyl)-4-pyrimidone
(j) 2-[3-(3-amino-2-pyridylmethylthio)propylamino]-5-(3-pyridylmethyl)-4-pyrimidone
(k) 2-[3-(3-hydroxy-2-pyridylmethylthio)-propylamino]-5-(3-pyridylmethyl)-4-pyrimidone
(l) 2-[3-(3-isothiazolylmethylthio)propylamino]-5-(3-pyridylmethyl)-4-pyrimidone
(m) 2-[3-(4-bromo-3-isothiazolylmethylthio)-propylamino]-5-(3-pyridylmethyl)-4-pyrimidone
(n) 2-[3-(3-(1,2,5)-thiadiazolylmethylthio)-propylamino]-5-(3-pyridylmethyl)-4-pyrimidone
(o) 2-[3-(4-chloro-3-(1,2,5)-thiadiazolylmethylthio)-propylamino]-5-(3-pyridylmethyl)-4-pyrimidone
(p) 2-[3-(5-amino-2-(1,3,4)-thiadiazolylmethylthio)-propylamino]-5-(3-pyridylmethyl)-4-pyrimidone

EXAMPLE 39

Substitution of 5-(4-imidazolyl)pentylamine for 3-(5-methyl-4-imidazolylmethylthio)propylamine in the procedure of Example 36 leads to the production of:
2-[5-(4-imidazolyl)pentylamino]-5-(3-pyridylmethyl)-4-pyrimidone

EXAMPLE 40

Pharmaceutical composition:

| Ingredients | Amounts |
| --- | --- |
| 2-[3-(5-methyl-4-imidazolylmethylthio)-propylamino]-5-(3-pyridylmethyl)-4-pyrimidone trihydrochloride | 75 mg |
| Sucrose | 75 mg |
| Starch | 25 mg |
| Talc | 5 mg |
| Stearic Acid | 2 mg |

The ingredients are screened, mixed and filled into a hard gelatin capsule.

EXAMPLE 41

Pharmaceutical composition:

| Ingredients | Amounts |
| --- | --- |
| 2-[3-(5-methyl-4-imidazolymethylthio)-propylamino]-5-(3-pyridylmethyl)-4-pyrimidone trihydrochloride | 100 mg |
| Lactose | 100 mg |

The ingredients are screened, mixed and filled into a hard gelatin capsule. Similarly, the other compounds of Formula 1 may be formulated into pharmaceutical compositions by the procedures of Examples 40 and 41.

The pharmaceutical compositions prepared as in the foregoing examples are administered to a subject within the dose ranges given hereabove to block histamine $H_2$-receptors.

EXAMPLE 42

(a) β-(6-Methyl-3-pyridyl)cinnamic acid, m.p. 213.5°–215.5°, was converted into the corresponding ethyl ester m.p. 36°–37° which was reduced to give ethyl β-(6-methyl-3-pyridyl)propionate (oil).

(b) Treatment of ethyl β-(6-methy-3-pyridyl)propionate with sodium and ethyl formate according to the procedure of Example 1(i) gave 5-(6-methyl-3-pyridylmethyl)-2-thiouracil m.p. 240°–241° which was converted into 5-(6-methyl-3-pyridylmethyl)-2-methylthio-4-pyrimidone m.p. 197°–198.5° by the procedure of Example 1(ii)

(c) Treatment of 5-(6-methyl-3-pyrimidylmethyl)-2-methylthio-4-pyrimidone with
(i) 2-(5-methyl-4-imidazolylmethylthio)-ethylamine
(ii) 2-(2-thiazolylmethylthio)ethylamine
(iii) 2-(3-bromo-2-pyridylmethylthio)ethylamine
(iv) 4-(5-methyl-4-imidazolyl)butylamine
according to the genral procedure of Example 1(iii) gave
(a) 2-[2-(5-methyl-4-imidazolylmethylthio)ethylamino]-5-(6-methyl-3-pyridylmethyl)-4-pyrimidone trihydrobromide m.p. 195.5°–198° (from ethanolic hydrogen bromide)

(b) 2-[2-(2-thiazolylmethylthio)ethylamino]-5-(6-methyl-3-pyridylmethyl)-4-pyrimidone trihydrochloride m.p. 187°-190°.

(c) 2-[2-(3-bromo-2-pyridylmethylthio)ethylamino]5-(6-methyl-3-pyridylmethyl)-4-pyrimidone trihydrochloride m.p. 193°-196°

(d) 2-[4-(5-methyl-4-imidazolyl)butylamino]-5-(6-methyl-3-pyridylmethyl)-4-pyrimidone trihydrochloride m.p. 189°-190°

EXAMPLE 43

(a) Ethyl 3-(3-pyridyl)crotonate (prepared from treating 3-acetylpyridine with ethoxycarbonylmethyltriphenylphosphonium bromide and sodium ethoxide) was hydrogenated in ethanol at 40 p.s.i. with 10% palladium on charcoal catalyst to give ethyl 3-(3-pyridyl)-butyrate, b.p. 74°/0.15 mmHg.

(b) Treatment of ethyl 3-(3-pyridyl)butyrate with ethyl formate and sodium hydride in glyme, followed by acidification gave ethyl 2-(hydroxymethyl)-3-(3-pyridyl)butyrate, m.p. 128°-131°.

(c) Treatment of ethyl 2-(hydroxymethyl)-3-(3-pyridyl)-butyrate with thiourea and sodium ethoxide, followed by acidification gave 5-(1-(3-pyridyl)ethyl)-2-thiouracil m.p. 225°-228°.

(d) Treatment of 5-(1-(3-pyridyl)ethyl)-2-thiouracil with methyl iodide and sodium ethoxide in ethanol at 0°, followed by acidification gave 2-methylthio-5-[1-(3-pyridyl)ethyl]-4-pyrimidone m.p. 201°-204°.

(e) Fusion of 2-methylthio-5-(1-(3-pyridyl)ethyl-4-pyrimidone at 160° with 2-(5-methyl-4-imidazolylmethylthio)ethylamine gave 2-[2-(5-methyl-4-imidazolylmethylthio)ethylamino]-5-(1-(3-pyridyl)ethyl)-4-pyrimidone which was converted into the trihydrochloride with hydrogen chloride which was recrystallised from methanol-ether and had m.p. 273°-275°.

Found: C, 44.8; H, 5.15; N, 17.4; S, 6.6; Cl, 22.4; $C_{18}H_{22}N_6OS \cdot 3HCl$. Requires: C, 45.05; H, 5.25; N, 17.5; S, 6.7; Cl, 22.2%

(f) Fusion of 2-methylthio-5-(1-(3-pyridyl)ethyl)-4-pyrimidone at 160° with (i) 2-(2-thiazolylmethylthio)ethylamine (ii) 2-(3-bromo-2-pyridylmethylthio)ethylamine leads to the production of (i) 2-[2-(2-thiazolylmethylthio)ethylamino]-5-(1-(3-pyridyl)ethyl)-4-pyrimidone (ii) 2-[2-(3-bromo-2-pyridylmethylthio)ethylamino]-5-(1-(3-pyridyl)ethyl)-4-pyrimidone

EXAMPLE 44

(a) A mixture of pyridine-3-carboxaldehyde (48 g), ethyl acetoacetate (52 g) aqueous piperidine acetate (40% 4.8 g) and 5% palladium on charcoal catalyst (50% wet, 2.48 g) was hydrogenated at 100 p.s.i. at 30° for 22 hours. The mixture was diluted with ether, filtered and the filtrate was evaporated and distilled under reduced pressure to give ethyl α-(3-pyridylmethyl)acetoacetate (b.p. 146°/1 mmHg). This ester was refluxed with thiourea and sodium ethoxide in ethanol, and the mixture was subsequently acidified to give 5-(3-pyridylmethyl)-6-methyl-2-thiouracil m.p. 328°-331°.

(b) Treatment of 5-(3-pyridylmethyl)-6-methyl-2-thiouracil with methyl iodide and sodium ethoxide in ethanol at 0° followed by acidification gave 2-methylthio-5-(3-pyridylmethyl)-6-methyl-4-pyrimidone m.p. 208°-211°.

(c) Fusion of 2-methylthio-5-(3-pyridylmethyl)-6-methyl-4-pyrimidone at 160°-170° with (i) 2-(2-thiazolylmethylthio)ethylamine (ii) 2-(3-bromo-2-pyridylmethylthio)ethylamine gave (i) 2-[2-(2-thiazolylmethylthio)ethylamino]-5-(3-pyridylmethyl)-6-methyl-4-pyrimidone, m.p. 159°-162°.

(ii) 2-[2-(3-bromo-2-pyridylmethylthio)ethylamino]-5-(3-pyridylmethyl)-6-methyl-4-pyrimidone, m.p. 118°-121°.

(d) Treatment of 2-methylthio-5-(3-pyridylmethyl)-6-methyl-4-pyrimidone with 2-(5-methyl-4-imidazolylmethylthio)ethylamine in refluxing pyridine for 25 hours, followed by evaporation of the mixture and chromatographic purification of the residue on silica gel (eluting with chloroform/methanol 5:1) gave 2-[2-(5-methyl-4-imidazolylmethylthio)ethylamino]-5-(3-pyridylmethyl)-6-methyl-4-pyrimidone m.p. 128°-131°.

EXAMPLE 45

Substitution of (a) 2-[2-(2-imidazolyl)ethylthio]ethylamine (b) 3-(2-imidazolylthio)propylamine (c) 3-(2-pyridylthio)propylamine (d) 3-(2-thiazolylthio)propylamine (e) 5-(4-imidazolyl)pentylamine for 2-(5-methyl-4-imidazolylmethylthio)ethylamine in the general procedure of Example 6(iii) leads to the production of (a) 2-[2-(2-(2-imidazolyl)ethylthio)ethylamino]-5-(3-pyridylmethyl)-4-pyrimidone (b) 2-[3-(2-imidazolylthio)propylamino]-5-(3-pyridylmethyl)-4-pyrimidone (c) 2-[3-(2-pyridylthio)propylamino]-5-(3-pyridylmethyl)-4-pyrimidone (d) 2-[3-(2-thiazolylthio)propylamino]-5-(3-pyridylmethyl)-4-pyrimidone (e) 2-[5-(4-imidazolyl)pentylamino]-5-(3-pyridylmethyl)-4-pyrimidone

EXAMPLE 46

Substitution of 4-(3-Methoxy-2-pyridyl)butylamine for 2-(2-thiazolylmethylthio)ethylamine in the procedure of Example 42(c) gave 2-[4-(3-methoxy-2-pyridyl)butylamino]-5-(6-methyl-3-pyridylmethyl)-4-pyrimidone trihydrochloride m.p. 209°-210°.

EXAMPLE 47

Pharmaceutical composition:

| Ingredients | Amounts |
| --- | --- |
| 2-[4-(3-methoxy-2-pyridyl)butylamino]-5-(6-methyl-3-pyridylmethyl)-4-pyrimidone trihydrochloride | 75 mg |
| Sucrose | 75 mg |
| Starch | 25 mg |
| Talc | 5 mg |
| Stearic Acid | 2 mg |

The ingredients are screened, mixed and filled into a hard gelatin capsule.

EXAMPLE 48

Pharmaceutical composition:

| Ingredients | Amounts |
| --- | --- |
| 3-[4-(3-Methoxy-2-pyridyl)butylamino]-5-(3-pyridylmethyl)-4-pyrimidone trihydro- | |

| Ingredients | Amounts |
| --- | --- |
| chloride | 75 mg |
| Sucrose | 75 mg |
| Starch | 25 mg |
| Talc | 5 mg |
| Stearic Acid | 2 mg |

The ingredients are screened, mixed and filled into a hard gelatin capsule.

What is claimed is:

1. A compound of the formula:

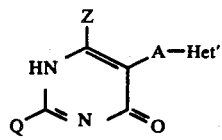

wherein Q is lower alkylthio, benzylthio, chloro or bromo; Z is hydrogen or lower alkyl; A is a straight or branched alkylene chain containing from 1-5 carbon atoms or $-(CH_2)_p W(CH_2)_q-$ where W is oxygen or sulphur and p and q are such that their sum is from 1 to 4; and Het' is a 5 or 6 membered hetercyclic ring selected from pyridine, pyridine-N-oxide, furan, thiophen, thiazole, oxazole, isothiazole, imidazole, pyrimidine, pyrazine, pyridazine or thiadiazole, which ring is optionally substituted by or or two (which may be the same or different) of the groups selected from lower alkyl, lower alkoxy, halo, hydroxy and amino, or Het' is a pyridine ring with a carbocyclic or cyclic ether ring containing two oxygen atoms fused to it, or Het' is a pyridine, imidazole or thiazole ring which has a benzene ring fused to it.

2. A compound of claim 1 in which Z is hydrogen, A is methylene and Het' is pyridine which is substituted by a lower alkyl, lower alkoxy, halo, hydroxy or amino group.

3. A compound of claim 1 in which Z is hydrogen, A is methylene and Het' is 2-pyridyl, 3-pyridyl or 4-pyridyl optionally substituted by lower alkyl or lower alkoxy.

4. A compound of claim 1 in which Het' is 3-pyridyl.

5. A compound of claim 1, said compound being 5-(6-methyl-3-pyridylmethyl)-2-methylthio-4-pyrimidone.

* * * * *

UNITED STATES PATENT AND TRADEMARK OFFICE
CERTIFICATE OF CORRECTION

PATENT NO. : 4,216,318

DATED : August 5, 1980

INVENTOR(S) : Thomas H. Brown, Graham J. Durant and Charon R. Ganellin

It is certified that error appears in the above-identified patent and that said Letters Patent are hereby corrected as shown below:

Column 5, line 54, that portion of the line reading (1) $HCO_2Et$, N    should read    (1) $HCO_2Et$, Na Column 7, lines 8-9, "vasodilation" should read -- vasodilatation -- .

Column 9, line 51, $99°$ should read $199°$ .

Column 13, line 13, 2-(4- should read 2-[2-(4- .

Signed and Sealed this

Twenty-eighth Day of October 1980

[SEAL]

Attest:

SIDNEY A. DIAMOND

Attesting Officer

Commissioner of Patents and Trademarks